United States Patent
Loomas et al.

(12)
(10) Patent No.: US 6,632,232 B1
(45) Date of Patent: *Oct. 14, 2003

(54) CORNEAL VACUUM CENTERING GUIDE AND DISSECTOR

(75) Inventors: Bryan Loomas, Santa Clara; James Davenport, Fallbrook; Mark Mathis, Fremont, all of CA (US)

(73) Assignee: Addition Technology, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/933,855

(22) Filed: Sep. 19, 1997

Related U.S. Application Data

(63) Continuation of application No. 08/401,465, filed on Mar. 9, 1995, now abandoned, which is a division of application No. 08/214,654, filed on Mar. 15, 1994, now Pat. No. 5,403,335, which is a continuation-in-part of application No. 07/867,745, filed on Apr. 10, 1992, now abandoned.

(51) Int. Cl.$^7$ ................................................ A61B 17/32
(52) U.S. Cl. ......................................... 606/166; 30/301
(58) Field of Search ............................. 606/1, 108, 166, 606/167, 184, 185; 604/22; 30/301

(56) References Cited

U.S. PATENT DOCUMENTS

| | | | |
|---|---|---|---|
| 2,249,906 A | | 7/1941 | Longoria |
| 3,074,407 A | * | 1/1963 | Moon et al. ............... 606/166 |
| 4,026,591 A | | 5/1977 | Cleaveland |
| 4,061,146 A | | 12/1977 | Baehr et al. |
| 4,319,575 A | | 3/1982 | Bonte |
| 4,417,579 A | | 11/1983 | Soloviev et al. |
| 4,423,728 A | | 1/1984 | Lieberman |

(List continued on next page.)

FOREIGN PATENT DOCUMENTS

| | | |
|---|---|---|
| DE | 3838253 | 5/1990 |
| SU | 1771730 A1 | 10/1992 |
| WO | WO 88/10096 | 12/1988 |
| WO | WO 89/00404 | 1/1989 |
| WO | WO 91/08711 | 6/1991 |

OTHER PUBLICATIONS

Blavatskaia, D.E. D. "The use of intralamellar homoplasty in order to reduce refraction of the eye" *Arch. Soc. Opthmol. Optom.* (1988) 6:319–325.

(List continued on next page.)

*Primary Examiner*—Kevin T. Truong
(74) *Attorney, Agent, or Firm*—Antoinette F. Konski

(57) ABSTRACT

This invention is a surgical device for producing a generally circular, interlamellar pathway within the corneal stroma of the eye. The device is made up of three major components: a vacuum centering guide having an inner bore which fits at one end against the front of the eye, a barrel which fits within the inner bore of the centering guide and to which is attached the third major component, a generally circular dissecting ring. The dissecting ring is shaped in such way that when an eye surgeon twists the barrel to which the ring is attached, the ring moves through the interlamellar space in the stroma producing the desired channel or pathway. The centering guide may optionally include a ring having one or more pins which firmly engage the cornea's epiphilium. The constituent parts of the surgical device, particularly the dissecting ring, also form a part of this invention.

A split ring, or intracorneal ring ("ICR"), is inserted into the intrastromal passageway produced by the inventive device. The ICR changes the shape of the cornea and, in doing so, provides a chosen measure of visual correction.

16 Claims, 11 Drawing Sheets

U.S. PATENT DOCUMENTS

| | | | |
|---|---|---|---|
| 4,429,696 A | | 2/1984 | Hanna |
| 4,452,235 A | | 6/1984 | Reynolds |
| 4,614,187 A | | 9/1986 | Mulhollan et al. |
| 4,619,259 A | | 10/1986 | Graybill et al. |
| 4,662,370 A | | 5/1987 | Hoffmann et al. |
| 4,688,570 A | | 8/1987 | Kramer et al. |
| 4,688,574 A | * | 8/1987 | Kramer et al. .............. 606/166 |
| 4,766,896 A | | 8/1988 | Pao |
| 4,796,623 A | | 1/1989 | Krasner et al. |
| 4,815,463 A | | 3/1989 | Hanna |
| 4,941,093 A | | 7/1990 | Marshall et al. |
| 4,997,437 A | | 3/1991 | Grieshaber |
| 5,011,498 A | | 4/1991 | Krumeich et al. |
| 5,090,955 A | | 2/1992 | Simon |
| 5,372,580 A | | 12/1994 | Simon et al. |

OTHER PUBLICATIONS

English translation of Brazilian Patent Application No. BR 8705060 (Mar. 21, 1989).

Hartmann, Chr., et al., "Intrastromale Implantation Eines Justierbaren Kunststoffringes Zur Hornhautrefraktionsanderrung", pp. 465–475.

D'Hermies et al., "Biocompatibility of a refractive intracorneal PMMA ring" *Fortschr Ophthalmol* (1991) 88:790–793.

English translation of Brazilian Patent Application No. BR 8705060 (Mar. 21, 1989).

Hartmann, Chr., et al., "Intrastromale Implantation Eines Justierbaren Kunststoffringes Zur Hornhautrefraktionsänderung", pp. 465–475. An English language translation of the article is attached.

F.D'Hermies, et al.; *Biocompatibility of a Refractive Intracorneal PMMA ring*; Fortschr Ophthamol (1991) 88:790–793.

Folha De S. Paulo; *Veneza Une Saga Celta E Informatica*; Ciencia; Sexta–feira, 28 de Junho de 1991; 4 pgs.

McGourty; The Daily Telegraph; *If You Need Glasses to Read This, It Could be Good News*; May 30, 1991; 4 pgs.

*Corneal Ring Corrects Vision*; Clinica Weekly; Issue 451: May $22^{nd}$ 1991.

Lawrence M. Fisher; *An Implant That Corrects the Cornea's Curvature*; Philadelphia Inquirer; May 26, 1991.

Lawrence M. Fisher; *An Implant That Corrects the Cornea's Curvature*; The New York Times; May 26, 1991.

Owen Craig; *Eye Implant Promises 'Reversible' Surgery*; Newscientist; Jun. 1, 1991 No 1771 Weekly.

*Vedere Bene Senza Lenti*; Tecnica Cirurgica Dagli USA; Venerdi 31 Maggio.

*Test for Cornea Implant*; Santa Rosa Press Democrat; May 24, 1991.

Folha De S. Paulo; Brasil Faz Teste Pioneiro Para Cura Da Miopia; Ciencia; Sexta feira, 28 de Junho de 1991.

* cited by examiner

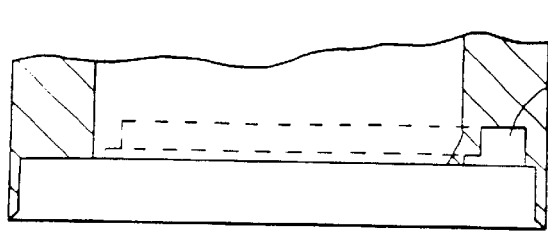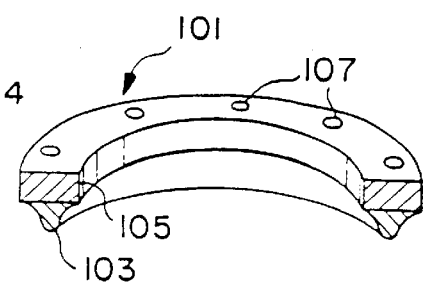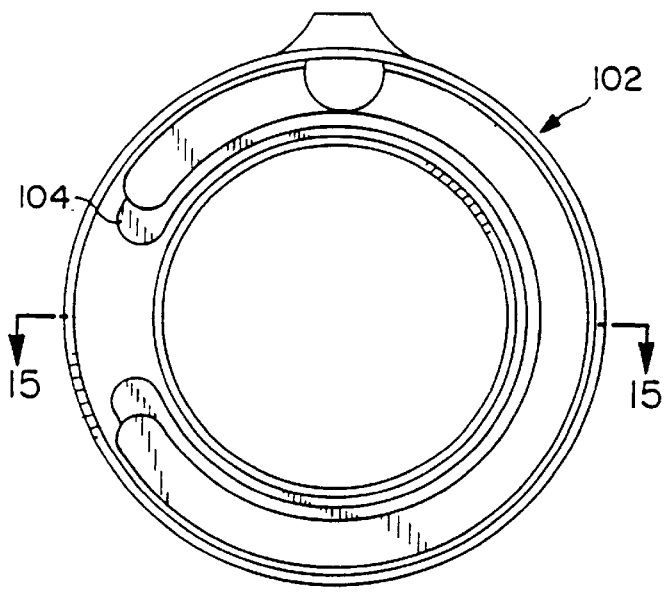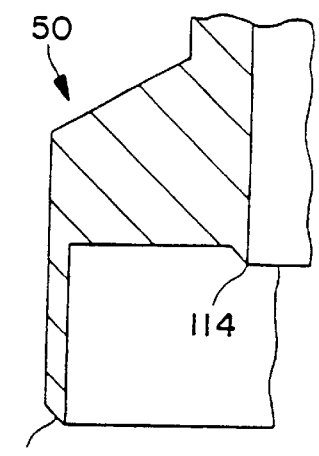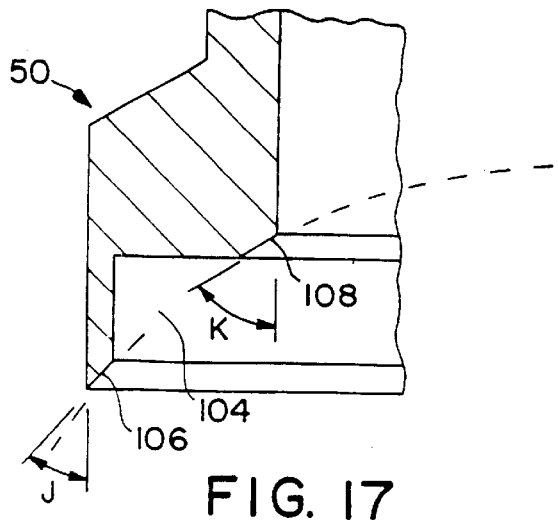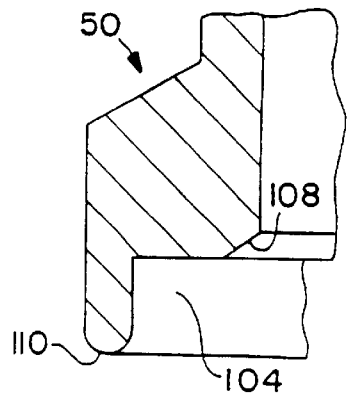
FIG. 15
FIG. 16
FIG. 14
FIG. 18
FIG. 17
FIG. 19

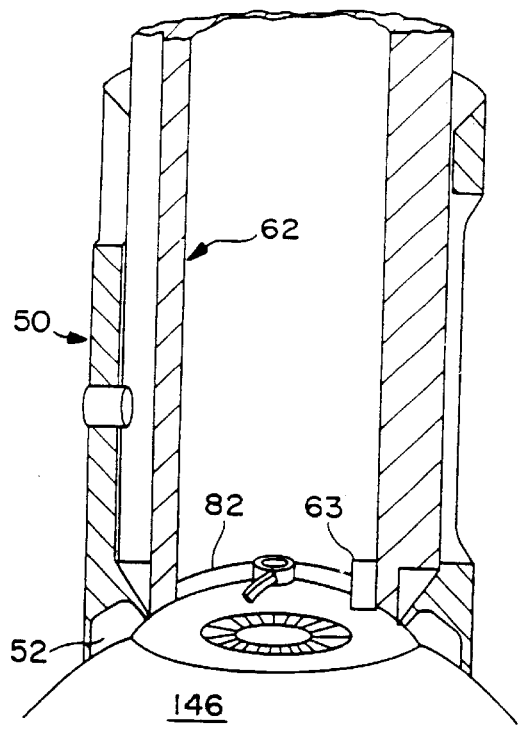
FIG. 26
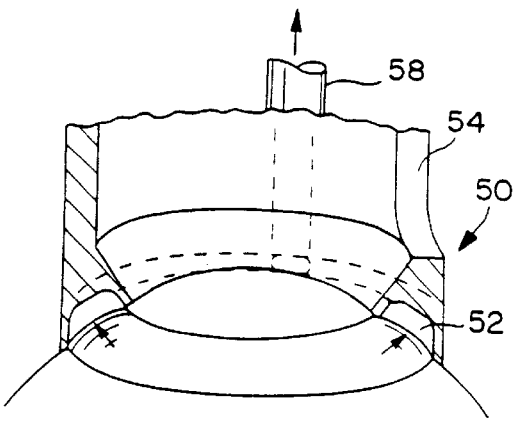
FIG. 27
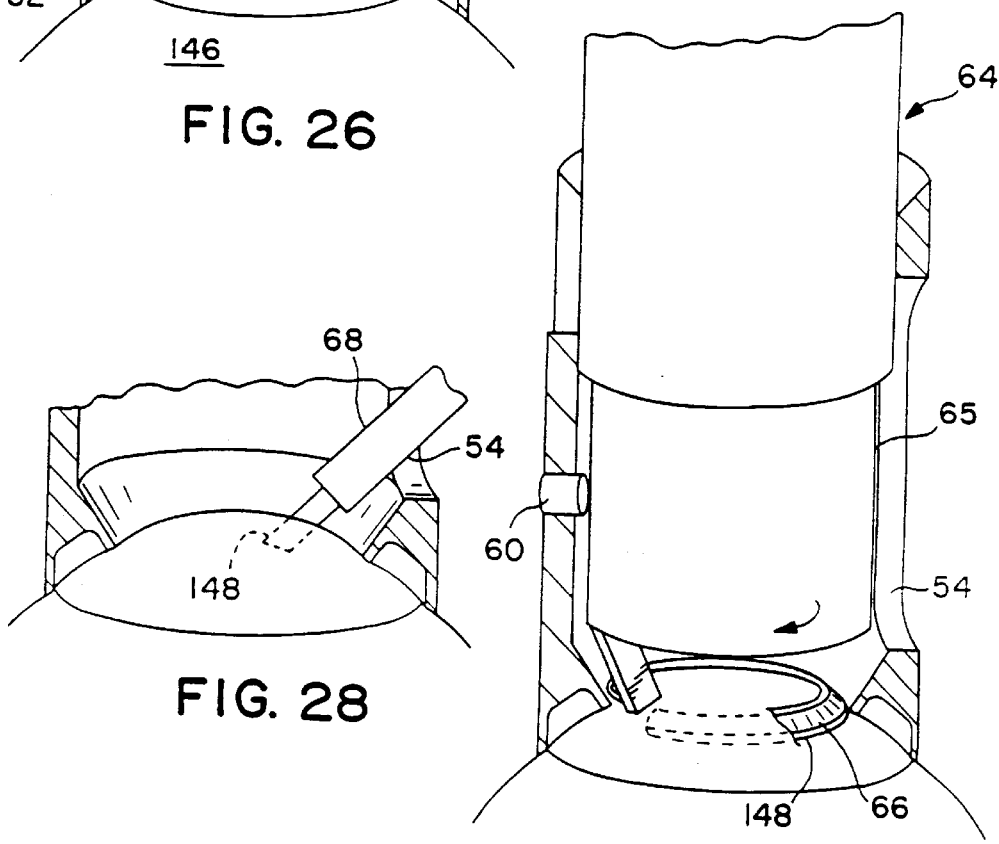
FIG. 28
FIG. 29

CORNEAL VACUUM CENTERING GUIDE AND DISSECTOR

This application is a continuation of application Ser. No. 08/401,465, filed Mar. 9, 1995, now abandoned; which is a divisional of Ser. No. 08/214,654, filed Mar. 15, 1994, now U.S. Pat. No. 5,403,335; which is a continuation-in-part of Ser. No. 07/867,745, filed Apr. 10, 1992, now abandoned.

FIELD OF THE INVENTION

This invention is a surgical device for producing a generally circular, interlamellar pathway within the corneal stroma of the eye. The device is made up of three major components: a vacuum centering guide having an inner bore which fits at one end against the front of the eye, a barrel which fits within the inner bore of the centering guide and to which is attached the third major component, a generally circular dissecting ring. The dissecting ring is shaped in such a way that when an eye surgeon twists the barrel to which the ring is attached, the ring moves through the interlamellar space in the stroma producing the desired channel or pathway. The centering guide may optionally include a ring having one or more pins which firmly engage the cornea's epiphilium. The constituent parts of the surgical device, particularly the dissecting ring, also form a part of this invention.

A split ring, or intracorneal ring ("ICR"), is inserted into the intrastromal passageway produced by the inventive device. The ICR changes the shape of the cornea and, in doing so, provides a chosen measure of visual correction.

BACKGROUND OF THE INVENTION

Anomalies in the overall shape of the eye can cause visual disorders. Hyperopia ("farsightedness") occurs when the front-to-back distance in the eyeball is too small. In such a case, parallel rays originating greater than 20 feet from the eye focus behind the retina. In contrast, when the front-to-back distance of eyeball is too large, myopia ("nearsightedness") occurs and the focus of parallel rays entering the eye occurs in front of the retina. Astigmatism is s condition which occurs when the parallel rays of light do not come to a single point within the eye, but rather have a variable focus due to the fact that the cornea is aspherical and refracts light in a difference meridian at different distances. Some degree of astigmatism is normal, but where it is too high, it must often be corrected.

Hyperopia, myopia, and astigmatism are usually corrected by glasses or contact lenses. Surgical methods for the correction of such disorders are known. Such methods include radial keratotomy (see, e.g., U.S. Pat. Nos. 4,185,463 and 4,688,570) and laser corneal Ablation (se, e.g., U.S. Pat. No. 4,941,093).

Another method for correcting those disorders is through the implantation of polymeric rings in the eye's corneal stroma to change the curvature of the cornea. Previous work involving the implantation of polymethylmethacrylate (PMMA) rings, allograft corneal tissue, and hydrogels is well documented. One of the ring devices involves a ring design that allows a split ring to be inserted into a channel dissected in the stromal layer of the cornea using a minimally invasive incision through which the channel for the implant is created and through which the implant is inserted.

U.S. Pat. No. 4,452,235, to Reynolds, describes a method and apparatus for corneal curvature adjustment. The method involves inserting one end of a split end adjusting ring into the cornea of the eye and moving the ring in a circular path until its ends meet. The ends are thereafter adjusted relative to each other until the shape of the eye has assumed a desired curvature whereupon the ends are fixedly attached to maintain the desired curvature of the cornea.

Although the procedure for introducing ICRs into the intracorneal stroma is known, our inventive insertion devices used to implement these procedures is not shown.

Vacuum devices useful for ocular surgical procedures are, however, common. For instance, U.S. Pat. No. 4,423,728, to Lieberman, shows a cam-guided trephine for selectively cutting a circular or V-shaped groove about the cornea. The device utilizes a pair of suction rings which affix the apparatus onto the sclera of the patient's eye. The vacuum is usually less than about 10 cm of water thereby avoiding raising the intraocular pressure above the physiological levels. The suction ring lies in the anatomically constant area just outside the limbus.

Similarly, U.S. Pat. No. 4,997,437 to Grieshaber, shows a process and apparatus for cornea grinding. The device has a base member which is held to the conjuctiva of the eye by vacuum space formed about the periphea of the cornea. A rotary grinder is attached to the base member and slides onto the eye through the interior bore of the base member. No provision is made for preventing rotation of the base member.

None of these disclosures shows the combination of devices similar to those disclosed herein.

Suggestion of blunt points or dissectors for producing channels within the interlamellar boundaries are found. See, for instance, U.S. Pat. No. 5,090,955, to Simon and "Intrastomale Implantation Eines Justierbaren Kunstofforings Zur Hornhau Trefraktion Sanderung", Hartmann et al., pp. 465–475. They do not suggest the special relationship shown with the dissector support.

An optional aspect of this invention is the use of pins which engage the front of the eye to prevent rotation of the inventive device during use.

U.S. Pat. No. 4,429,696, to Hanna, shows a surgical apparatus for precisely cutting out the cornea of the eye by making at least one circular incision. The device is held to the front of the eye by a series of claws, which optionally may be retractable, and suction placed on the central portion of the eye during the cutting operation. There is no suggestion of using the claws in cooperation with an annular vacuum ring.

Finally, the invention may optionally include a soft base conformable to the surface of the eye.

Such devices are known. See, for example, published PCT Application WO91/08711, to Kilmer et al., shows a device for re-profiling a cornea. The device rests on a resilient vacuum ring which is adapted to sit on the sclera portion of an eye which surrounds the cornea which is to be re-profiled. The top side of the vacuum ring has a number of positioning pins which allow it to be connected to the remainder of the profiling apparatus.

The invention described herein is a device for producing in the corneal stroma, the circular pathway needed for the insertion of the ICR using a suction ring which detachably adheres to the front of the eye.

BRIEF DESCRIPTION OF THE DRAWINGS

FIG. 14 is a bottom view of a variation of the invention also utilizing multiple vacuum chambers.

FIG. 15 is a partial side cross-sectional view of the variation shown in FIG. 14.

FIG. 16 shows a soft insert suitable for producing a vacuum on the front of the eye.

FIGS. 17, 18 and 19 are enlarged side cross-sectional views of peripheral or outer edge of the vacuum base where they would meet the surface of the eye during use.

FIGS. 26, 27, 28, 29 and 30 depict the steps of using the inventive device to prepare the eye and install the ICR in the corneal stroma.

DESCRIPTION OF THE INVENTION

Prior to explaining the details of the inventive devices, a short explanation of the physiology of the eye is needed to appreciate the functional relationship of the device to the eye.

Figure 1:
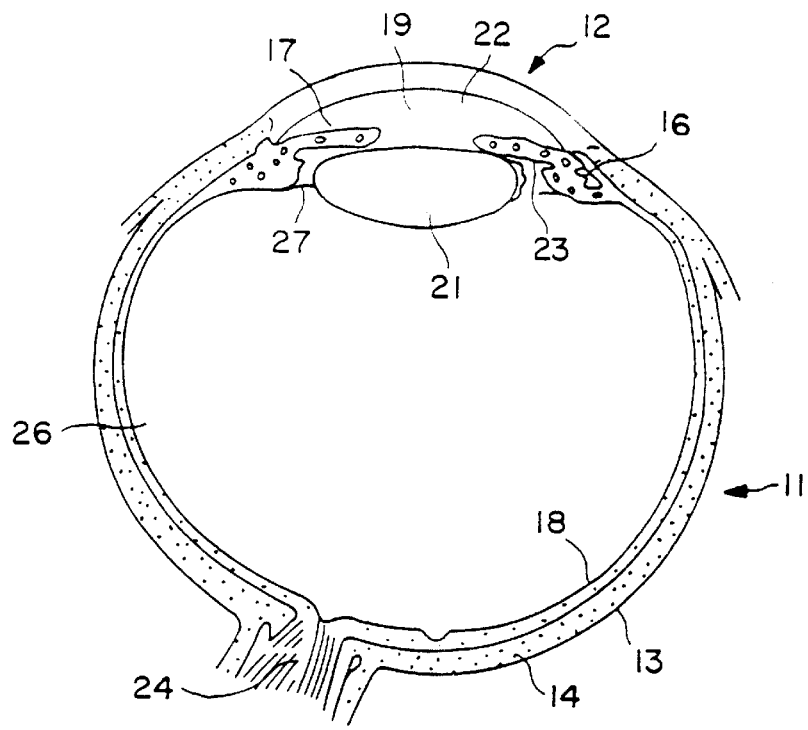
FIG. 1 is a horizontal section of an eye.

FIG. 1 shows a horizontal section of the eye with the globe 11 of the eye resembling a sphere with an anterior bulged spherical portion representing the cornea 12.

The globe 11 of the eye consists of three concentric coverings enclosing the various transparent media through which the light must pass before reaching the sensitive retina 18. The outermost covering is a fibrous protective portion, the posterior five-sixths of which is white and opaque and called the solora 13, and sometimes referred to as the white of the eye where visible to the front. The anterior one-sixth of this outer layer is the transparent cornea 12.

A middle covering is mainly vascular and nutritive in function and is comprised of the choroid 14, ciliary body 16 and iris 17. The choroid 14 generally functions to maintain the retina 18. The ciliary body 16 is involved in suspending the lens 21 and accommodation of the lens. The iris 17 is the most anterior portion of the middle covering of the eye and is arranged in a frontal plane. It is a thin circular disc corresponding to the diaphragm of a camera, and is perforated near its center by a circular aperture called the pupil 19. The size of the pupil varies to regulate the amount of light which reaches the retina 18. It contracts also to accommodation, which serves to sharpen the focus by diminishing spherical aberration. The iris 17 divides the space between the cornea 12 and the lens 21 into an anterior chamber 22 and posterior chamber 23. The innermost portion of covering is the retina 18, consisting of nerve elements which form the true receptive portion for visual impressions.

The retina 18 is a part of the brain arising as an outgrowth from the fore-brain, with the optic nerve 24 serving as a fiber tract connecting the retin part of the brain with the fore-brain. A layer of rods and cones, lying just beneath a pigmented epiphilium on the anterior wall of the retina serve as visual cells or photoreceptors which transform physical energy (light) into nerve impulses.

The vitreous body 26 is a transparent gelatinous mass which fills the posterior four-fifths of the globe 11. At its sides it supports the ciliary body 16 and the retina 18. A frontal saucer-shaped depression houses the lens.

The lens 21 of the eye is a transparent bi-convex body of crystalline appearance placed between the iris 17 and vitreous body 26. Its axial diameter varies markedly with accommodation. A ciliary zonule 27, consisting of transparent fibers passing between the ciliary body 16 and lens 21 serves to hold the lens 21 in position and enables the ciliary muscle to act on it.

Referring again to the cornea 12, this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
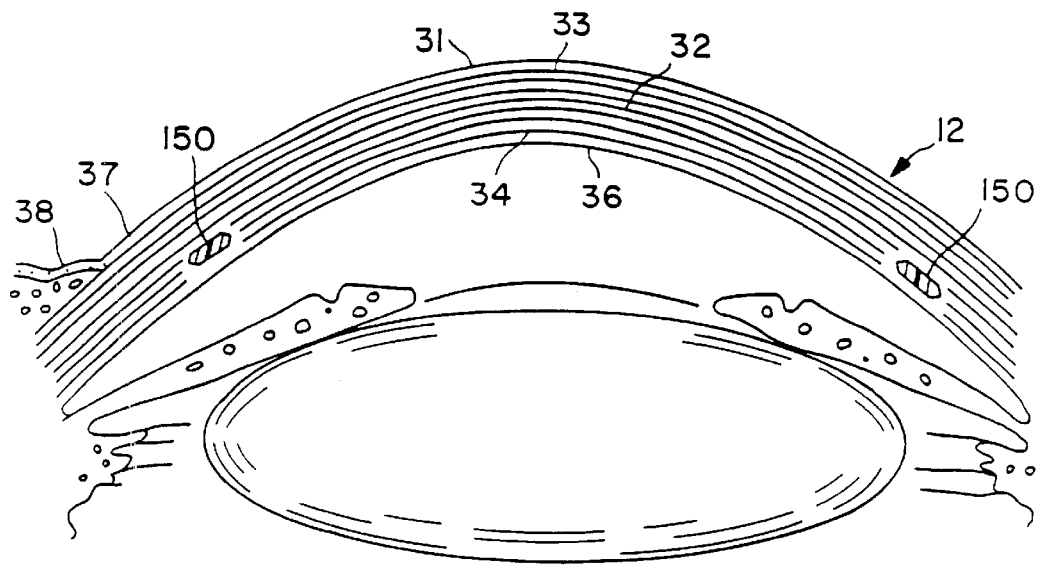
FIG. 2 is a horizontal section of the anterior portion of an eye.

Referring to FIG. 2, a more detailed drawing of the anterior portion of the globe, shows the various layers of the cornea 12 comprising an epithelium 31. Epithelial cells on the surface thereof function to maintain transparency of the cornea 12. These epithelial cells are rich in glycogen, enzymes and acetylcholine and their activity regulates the corneal corpuscles and controls the transport of water and electrolytes through the lamellae of the stroma 32 of the cornea 12.

An anterior limiting lamina 33, referred to as Bowman's membrane or layer, is positioned between the epiphilium 31 and the stroma 32 of the cornea. The stroma 32 is comprised of lamella having bands of fibrils parallel to each other and crossing the whole of the cornea. While most of the fibrous bands are parallel to the surface, some are oblique, especially anteriorly. A posterior limiting lamina 34 is referred to as Descemet's membrane. It is a strong membrane sharply defined from the stroma 32 and resistant to pathological processes of the cornea.

The endothelium 36 is the most posterior layer of the cornea and consists of a single layer of cells. The limbus 37 is the transition zone between the conjunctive 38 and sclera 13 on the one hand and the cornea 12 on the other.

Figure 3:
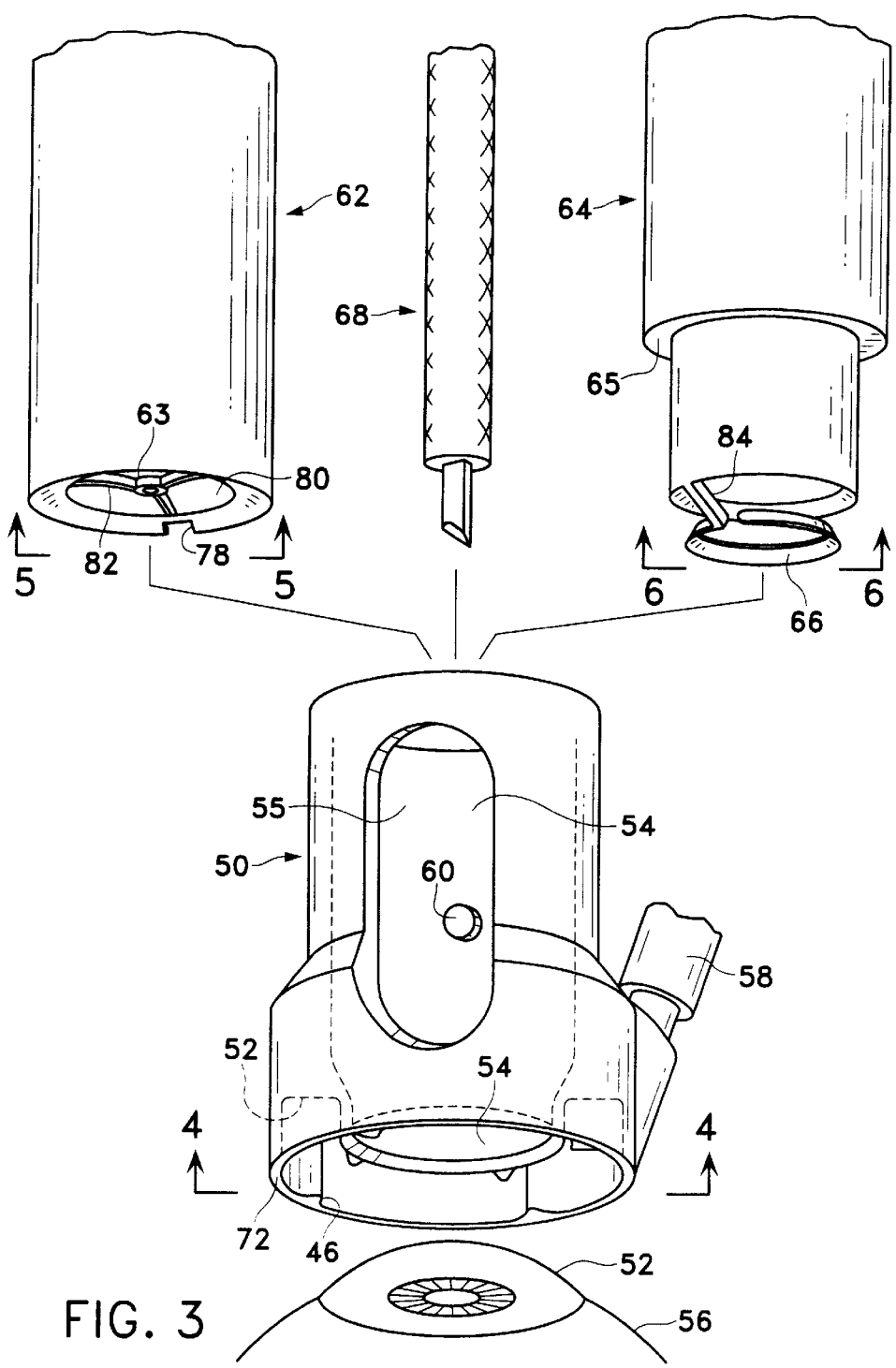
FIG. 3 is a front perspective view of the constituent parts of the invention vacuum device and their relationship to the eye during use.

FIG. 3 shows the various components used in this inventive surgical device. The support base (50), includes an annular circumcorneal vacuum ring (52) at the end proximal the cornea and a cylindrical or central bore (54) extending from the end of the support base distal the eye (56). The support base (50) typically contains a viewing port (55) through the extension wall of the base to allow the surgeon to make the initial incision into the eye and to clearly view the operational steps which take place at the corneal surface. The vacuum is brought in from vacuum source line (58). The circumcorneal vacuum ring (52) is configured so that it meets with and seals to the front of the eye rendering the support base (50) relatively immobile when the support base is applied to the front of the eye (56) and a suitable vacuum is applied to the vacuum source line (58). The vacuum chamber forms an annular vacuum space against the front of the eye. The support base (50) may also have a pin (60) which serves as an antirotatory device for corneal centering guide (62). Also shown in FIG. 3 is the incisor blade (68) which is inserted by the surgeon through the viewing port (55). An incision blade (68) is of a size and configuration which allows the knife to enter the cornea at a depth and angle suitable for later introduction of the dissector blade (66) into the intracorneal stroma.

Figure 4:
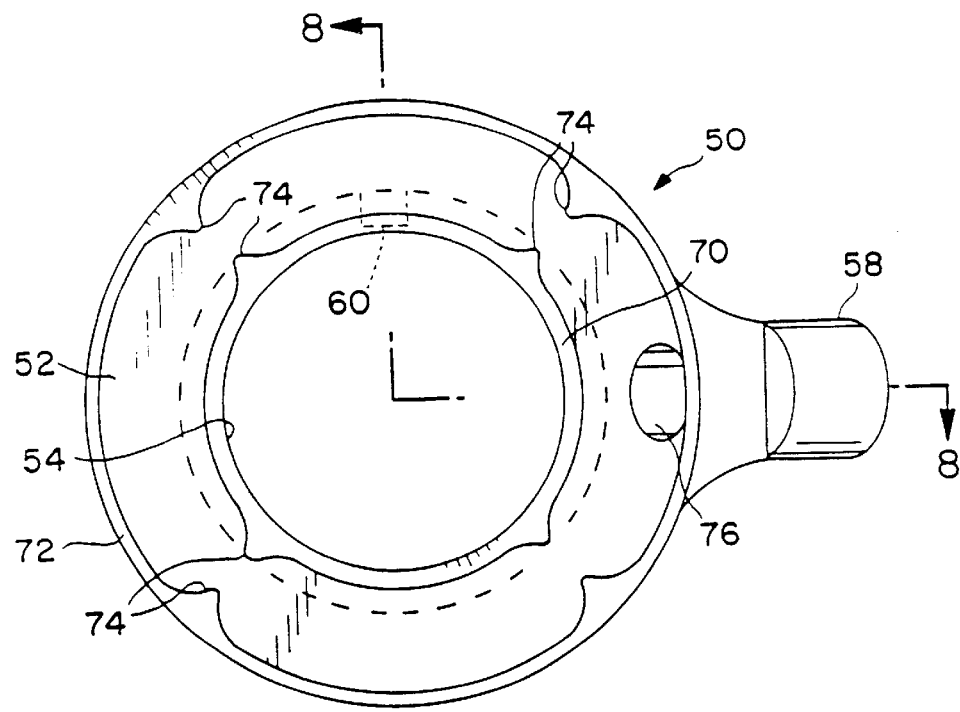
FIG. 4 is a bottom view of the base of the vacuum device.

FIG. 4 shows a bottom view of support base (50) in which the circumcorneal vacuum ring (52) may be clearly viewed. The circumcorneal vacuum ring (52) is made up of an inner wall (70) terminating on its inside by the central bore (54). The central bore (54) is at least large enough to see the entirety of the dissector blade (66) as is discussed below. The central bore (54) has an axis which substantially coincides with the axis of the dissector blade. The central bore (54) is desirably of a length such that the ratio of the bore's length to its diameter is between 0.25:1 and 15:1; specifically between 0.4:1 and 1:1; at least about 1:1 and less than about 3:1; or at least about 3:1 up to about 15:1. Preferably, the ratio is about 2.5:1. This sizing allows easy manipulation by the surgeon. The outer vacuum ring wall (72) desirably forms the outside of the support base (50). Interior to the circumcorneal vacuum ring (52) may be one or more ridges (74) which extend down to the corneal surface when the support base is attached to the guide. The ridges are positioned within the circumcorneal vacuum ring (52) to prevent rotation of the support base (50) during any surgical operation. Variations of the ridge design will be discussed below with regard to FIGS. 20 through 23. The opening (76) to the vacuum source line (58) is shown in FIG. 4.

Figure 5:
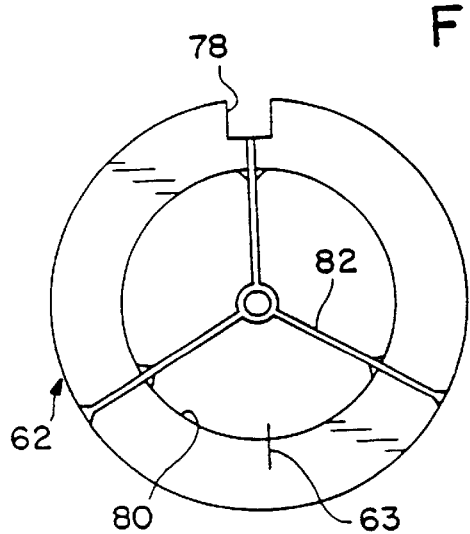
FIG. 5 is a bottom view of the centering insert for the inventive device.

FIG. 5 shows a bottom view of corneal centering and fixation guide (62). This guide (62) fits down within the inner barrel (54) of support base (50) and a groove (78) within the outer surface of the guide slides over and engages pin (60). In this way, corneal center and fixation guide (62) does not rotate with respect to support base (50). The inside bore (80) and the reticle are used to allow centering of the support base (50) about the cornea and to allow making a marking cut with incision marker (63). Once the surgeon determines that the support base (50) is properly centered by using the corneal centering and fixation guide (62), vacuum is applied through vacuum source line (58) and its terminal opening (76) in the circumcorneal vacuum ring (52).

Once support base (50) is affixed to the front of the eye, the corneal centering and fixation guide (62) is removed from the center bore (54) of the support base (50) and the incision for insertion of the dissector blade (66) is made. After the initial incision is completed, the dissector barrel (64) is inserted down into the inner bore (54) of the support base (50). The dissector blade (66) is attached to the dissector barrel (64) by dissector blade support arm (84). As the barrel rotates, it defines a barrel axis. The barrel axis is coincident to the blade axis discussed below.

Figure 7:
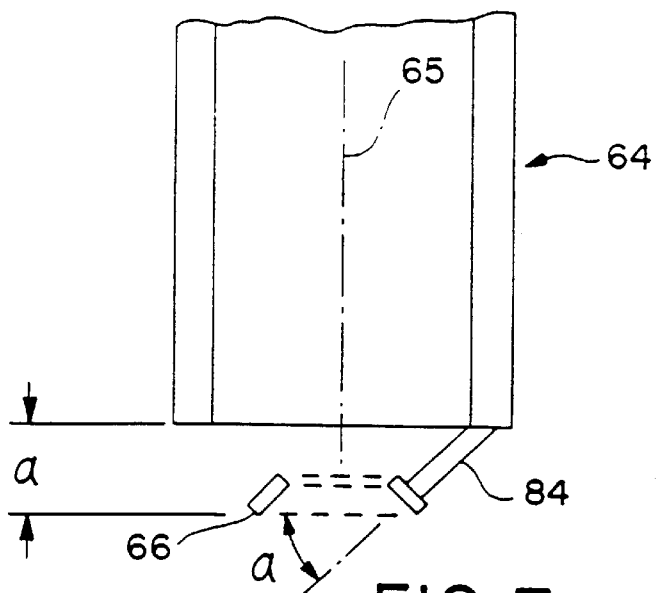
FIG. 7 is a side view of the dissector blade.
Figure 7A:
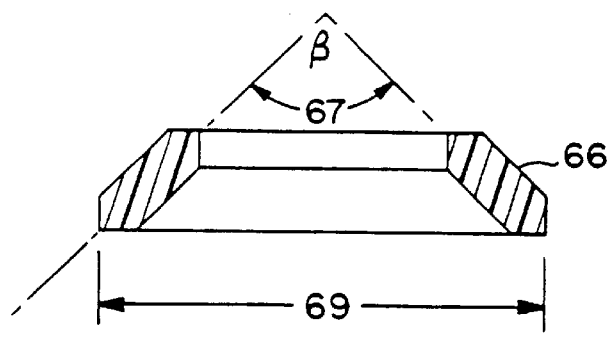
FIG. 7a is a side cross-section of the dissector blade.

FIG. 7 shows the desired features of the dissector blade (66) in greater detail. The blade, in cross-section, is desirably rectangular in cross-section. This permits a large amount of material to be incorporated in the blade and yet form a substantially rectangular path in the interlamellar spaces of the corneal stroma. The blade (66) as was shown above, is in the shape of a major arc of up to 350° having as its center the axis (65) as shown in FIG. 7. The blade's major arc is in a plane perpendicular to that axis (65). The blade may be tapered on its smaller edge as is shown in FIG. 7a and indeed may be of any convenient shape although we have found the two noted cross-sectional shapes (i.e., rectangular or hexagonal in which two opposite sides are longer than the remaining four) to be preferred. FIG. 7a shows the cone angle (67) of the dissector blade as is discussed below and the diameter (69) of the dissector blade (66). This diameter is preferably viewable through the upper end of the dissector barrel (64).

Figure 6:
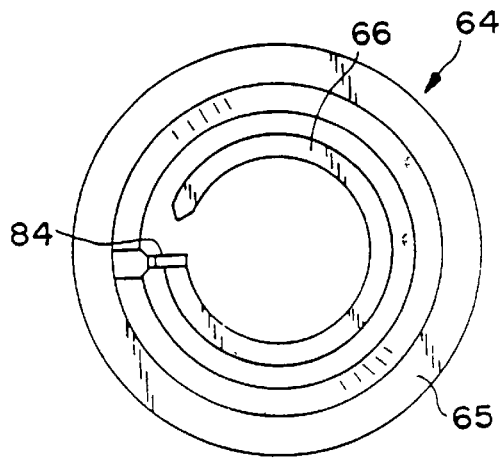
FIG. 6 is a bottom view of the dissector and its supporting insert barrel as used in the inventive device.

The blade is formed so that the dissector blade support arm (84) is at an angle $\alpha$ of up to about 90°. The angle of the blade support arm (84) to the plane of the blade (66) may be a value of 0° to 90°. It is preferably between 0° and 80°, more preferably the angle is 10°–50° and most preferably about 34° (±5°) to the plane of dissector blade (66). This angle results in the dissector blade support arm (84) being generally perpendicular to the cornea when it is inserted into the incision provided for introduction of the dissector blade (66) into the corneal stroma. This angle, although not absolutely critical, is desirable and has been found to prevent tearing of the epiphilium during the corneal operation. The length of blade angle support arm (84) is sufficient that the entire dissector blade is visible through the top of the dissector barrel during use—see FIG. 6. As was noted with regard to FIG. 3, the outer diameter of the dissector barrel (64) is the same as the bore (54) of the base (50). The overall relationship of the sizes of the diameter of the arc (69) of the blade to the length of the dissector barrel is desirably chosen so that the ratio of that length to the arc diameter is between 0.25:1 and 15:1; specifically between 0.4:1 and 1:1, at least about 1:1 and less than about 3:1; and at least about 3:1 but less than 15:1. Again these ratios allow ease of manipulation by the surgeon.

The dissector blade (66) has two other physical parameters which we believe to be important to the effective operation of the support base (50) in providing an interlamellar channel in the corneal stroma. Upon rotation of the dissector barrel (64), the dissector blade (66) must move in a path which is substantially planar. That is to say the path of the dissector blade (66) as it moves in the corneal intrastromal lamellar space described above, must not vary either up or down during the dissector barrel (64) rotation. The distance "a" shown in FIG. 7 is a constant. The blade can be considered to be in a plane which is perpendicular to the axis (65) which forms the center of ring (66).

Similarly, the cone angle $\beta$ (67) is preferably 112° (±30°). Again, this permits the dissector blade (66) to produce a channel which is parallel to the lamella found in the corneal stroma. The cone angle $\beta$ may, of course, vary a few degrees dependent on such variables as the geometry of the ICR installed, the size of the eye, and the amount of correction required.

Figure 7B:
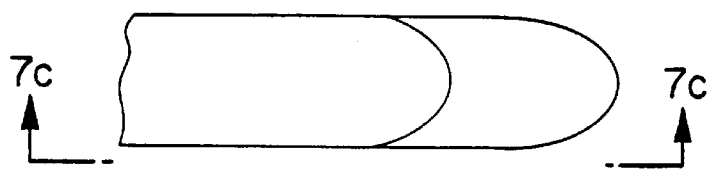
FIGS. 7b and 7c are top and side views of the tip of the dissector blade.
Figure 7C:

FIGS. 7b and 7c show one desired tip configuration of the dissector blade (66). We have found that a comparatively blunt but rounded device will provide an intrastromal channel fairly precisely in a constant depth within the lamella. Sharper blades have a tendency to cut through the lamella and produce a less desirable intrastromal channel.

Figure 8:
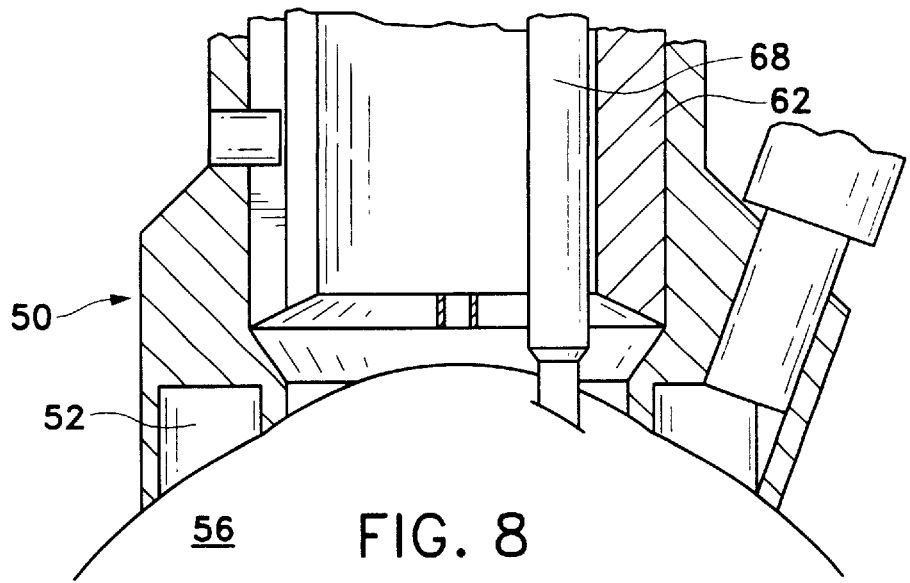
FIG. 8 is a side cross-section view of the vacuum device in place on the eye during the step of making the initial incision for later installation of an ICR.

FIG. 8 shows in a cross-section the step of creating the incision in the front of the eye using knife (68). The support base (50) secured by circumcorneal vacuum ring (52) is in place as is the corneal centering and fixation guide (62). The knife (68) has been brought down through the corneal centering and fixation guide (62) into the epiphilium and the stroma of the eye (56).

Figure 9:
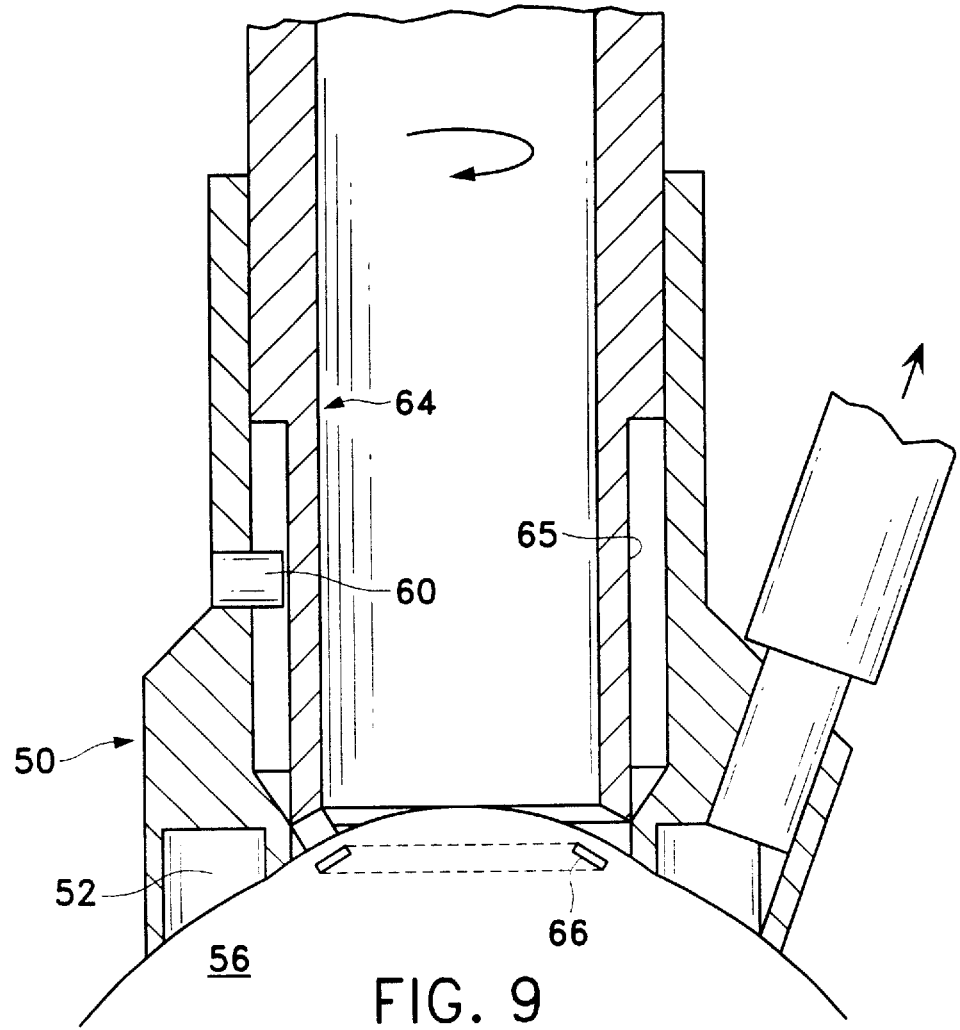
FIG. 9 is a side cross-sectional view of the vacuum device in place during the step of dissecting a circular channel in the corneal stroma.

Once the steps of centering and initial incision are complete, the corneal centering and fixation guide (62) and knife (68) are removed and the step shown in FIG. 9 is carried out.

In FIG. 9, again the support base (50) is in place on the front of the eye (56) secured by the vacuum in circumcorneal vacuum ring (52). The dissector barrel (64) having dissector blade (66) on its lower end is introduced into the inner bore of the support base (50). The leading edge of the dissector blade is introduced into the incision made during the step shown in FIG. 8 and the dissector barrel is rotated as shown. The dissector barrel is rotated far enough to make a full circular channel or until the dissector blade support arm (84) reaches the insertion made into the eye. Further rotation would cause tearing of the eye.

The dissector blade is then rotated in an opposite direction so to remove the dissector blade (6) from the channel it has just produced. We have also found it desirable to complete the interlamellar channel by using another dissector barrel which rotates in the opposite direction.

The ICR may be introduced as described below.

Figure 11:
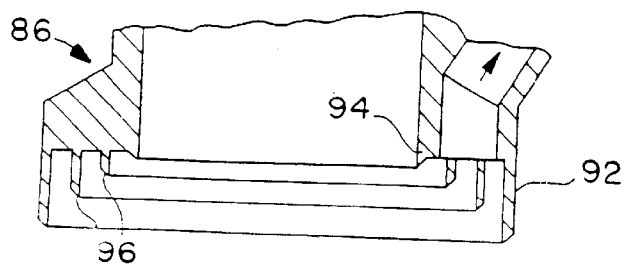
FIG. 11 is a side cross-section view of the inventive variation shown in FIG. 10.
Figure 10:
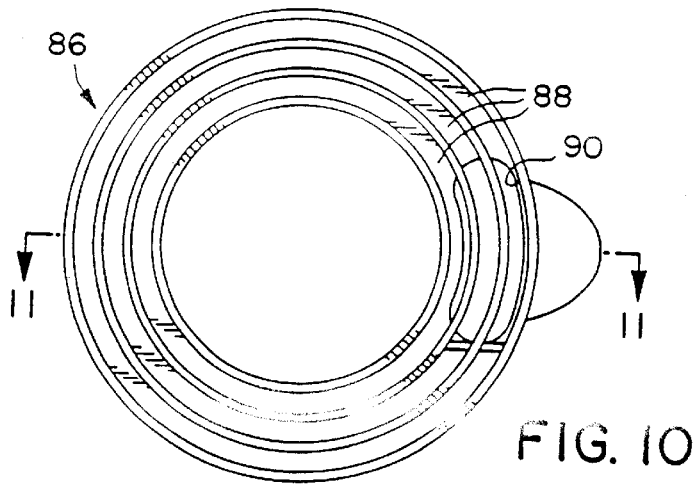
FIG. 10 is a bottom view of a variation of the invention utilizing multiple vacuum chambers.

The circumcorneal vacuum ring may be produced in a variety of desired arrangements. For instance, in FIGS. 10 and 11, a multi-chambered device is shown. In FIG. 10, a bottom view of the support base (86) is found. The circumcorneal vacuum ring is made up of three distinct chambers (88), each of which are connected to the vacuum source line opening (90). This variation is desired when additional support is needed between the outer support base wall (92) and the support base inner bore (94). Because the force applied to the eye is proportional to the area subjected to vacuum on the front of the eye, this variation can be used to additional area under vacuum to the device without trauma to the eye. As may be seen in FIG. 11, the various interior walls (96) are of a different height allowing them to conform to the front of the eye.

Figure 13:
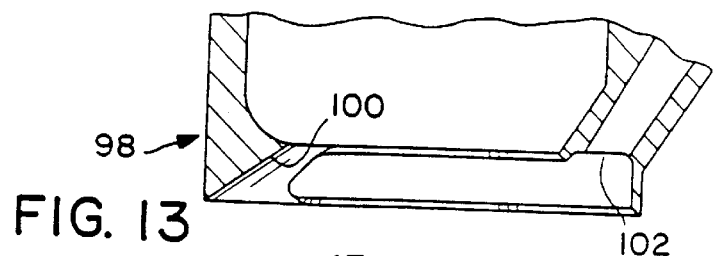
FIG. 13 is a partial side cross-sectional view of a variation of the invention shown in FIG. 12.
Figure 12:
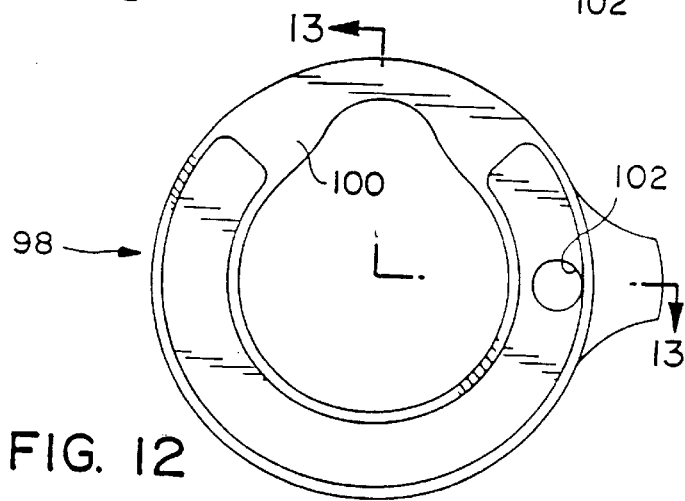
FIG. 12 is a bottom view of a variation of the invention utilizing a single chamber in the base.
Figure 21:
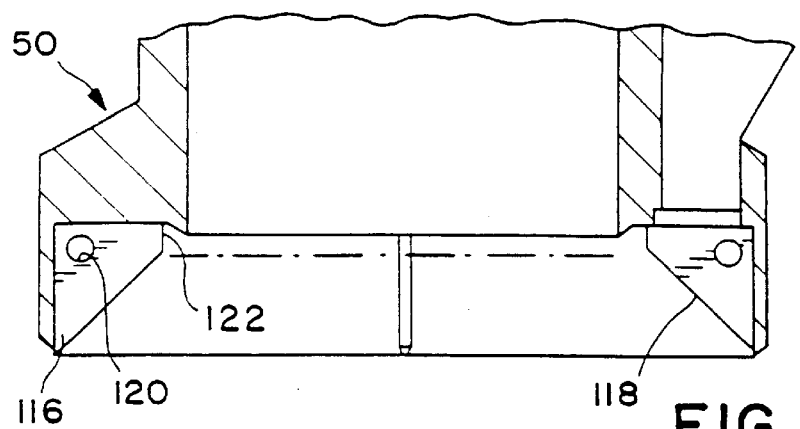
FIGS. 21, 22 and 23 show partial cross-sectional views of three variations of the radial wall devices placed in the vacuum chamber shown in FIG. 19.

FIGS. 12 and 13 show, respectively, a bottom view and a side partial cross-sectional view of another variation of the support base (98) in which the circumcorneal vacuum ring does not completely encircle the cornea. This configuration allows the viewing port (as shown in FIG. 3 as (55)) to be quite large and allows the surgeon views of the cornea both from above through the inner bore of the dissector barrel or through the side viewing port during the production of the inner stromal channel. Specifically, the open part of the channel meets the eye at surface (100) and the vacuum source line opening provides a vacuum source to the opening which fits against the eye. Support base (102), as is shown in FIGS. 14 and 15, is a multi-chamber device analogous to that found in FIGS. 12 and 13. The device and added upper chamber (104) allow the vacuum to more easily circumnavigate the cornea.

FIG. 16 shows a side perspective cross-section of an insert (101) which is suitable for inclusion in the lower end of the support base. This insert has a support ring (105) which may be metal, stiff plastic or other suitable material. A rubber seal (103) which fits against the edge is bonded to the support ring (105). The support ring may have holes (107) inserted therein so to allow vacuum access when the insert is placed into a support such as that shown in FIGS. 20–23.

FIGS. 17, 18 and 19 show three variations of the surfaces which are desirably used as the surfaces which meet the cornea in the circumcorneal vacuum ring. Specifically, FIGS. 17–19 are partial cross-sections of the vacuum chambers showing various edges of the circumcorneal vacuum chamber where the edges meet the surface of the eye. Specifically, FIG. 17 shows a variation in which the circumcorneal chamber (104) has an outer surface (106) which is disposed at an angle J such that J which is the angle which a tangent to a patient's cornea would make at that point. Similarly, inner chamber edge (108) is cut at an angle K such that the inner chamber edge (108) would lie substantially flat against the patient's cornea. In FIG. 18, the vacuum chamber (104) has an outer rounded chamber edge (110) and an inner chamber edge (108) which is similar in design to the variation shown in FIG. 17. The FIG. 19 variation uses an outer chamber (112) which is somewhat sharper but is not so sharp as to cause substantial trauma or cutting of the corneal surface. The inner chamber edge (114) is of a similar shape.

The vacuum chamber walls, the circumcorneal rings, and the support base may be made of a variety of materials including various plastics, metals, and pliable materials such as natural and synthetic rubbers.

Figure 20:
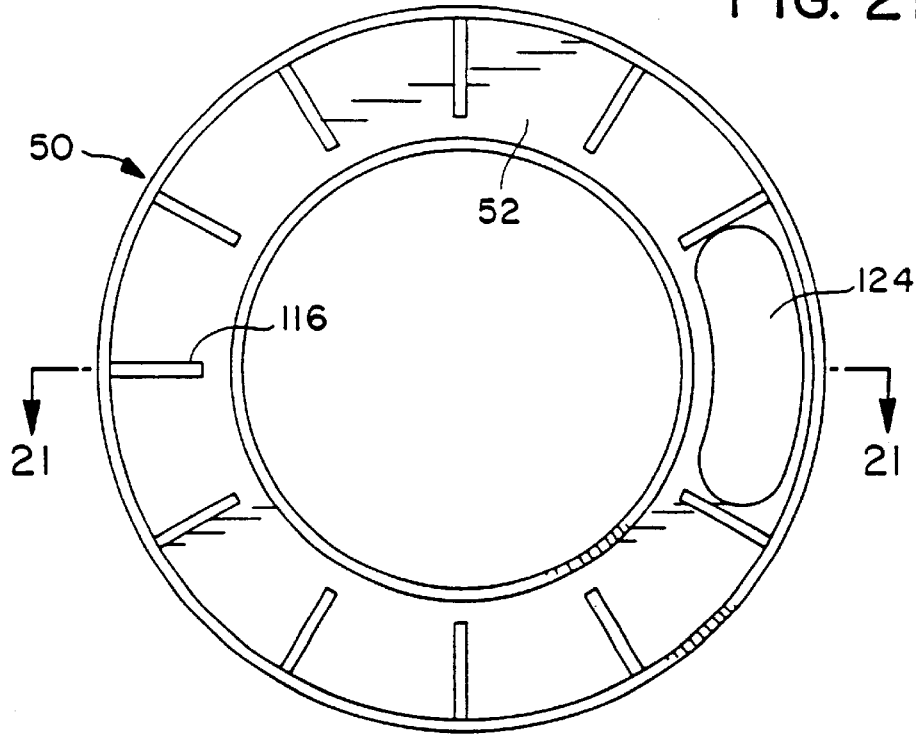
FIG. 20 shows a bottom view of a variation of the device which incorporates radial walls within the vacuum chamber to help prevent rotation of the vacuum base during ophthalmic operations.
Figure 22:
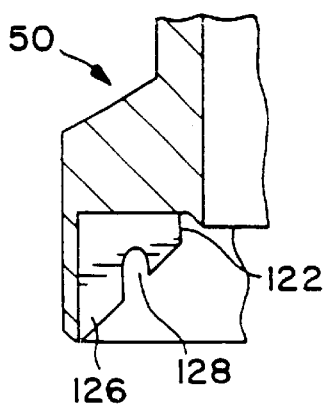

The preferred variant of the circumcorneal vacuum ring contains a number of ridges or vanes which serve to help prevent rotation of the support base during the ophthalmic operation. There are a number of suitable ways of introducing such anti-rotating features. For instance, in FIG. 3, short ridges (116) are included both in the inner and outer walls of the circumcorneal vacuum ring (52). The lower terminus of these short vanes (116) rest against the cornea and after vacuum is applied to the vacuum ring (52), the cornea is drawn up into the space surrounding the vanes (16) and the vanes prevent the support base from rotating. FIGS. 20–23 show other versions of vanes suitable for preventing rotation of the support base (50). FIG. 20 shows a bottom view of support base (50) in which eleven vanes (116) are interposes within the circumcorneal vacuum ring (52). As is shown in partial cross-section of the rendition shown in FIG. 20, the vanes have several identifying features. The surface (118) must meet the surface of the cornea after the suction is applied to the ring. There are pathways variously through the opening (120) and the stub wall (122) which allow the vacuum to be distributed from the vacuum line opening (124) to be distributed evenly about the full circumference of the circumcorneal vacuum chamber. The pathways for the distribution of the vacuum around the chamber is not critical. Multiple vacuum inlets are suitable and other channel shapes are appropriate. FIG. 22 shows still another variation of the vacuum chamber vane (126) also utilizing a stub wall (122) to allow vacuum distribution. The vacuum chamber vane (126) uses an additional slot (128) to distribute the vacuum. Once again, however, the lower surface of the vane meets flush with the eye and forms small indentations within the cornea once vacuum is applied.

Figure 23:
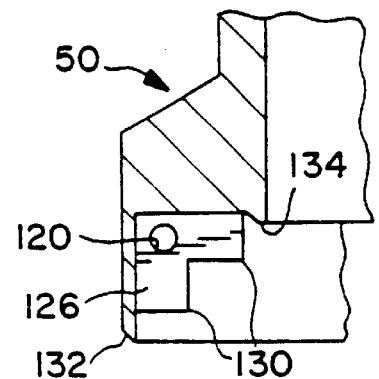

FIG. 23 shows a variation in concept for vane shape. The variation, instead of providing for flat surface against the cornea instead is stepped in such a way that small points (130) which are cut into the vane (126) engage the cornea when vacuum is applied to the device. Vacuum is distributed through hole (120) and in the spaces formed between outer wall (132) and the lower vane point, the space between the two vane points (130) and the space between the upper vane point (130) and the inner wall (134).

Figure 25:
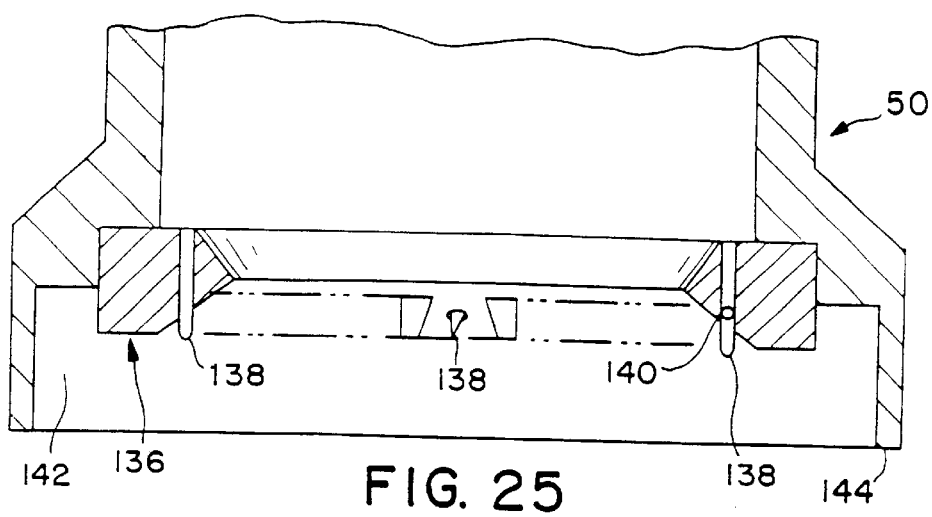
FIG. 25 is a side view cross-section of the device of FIG. 24.
Figure 24:
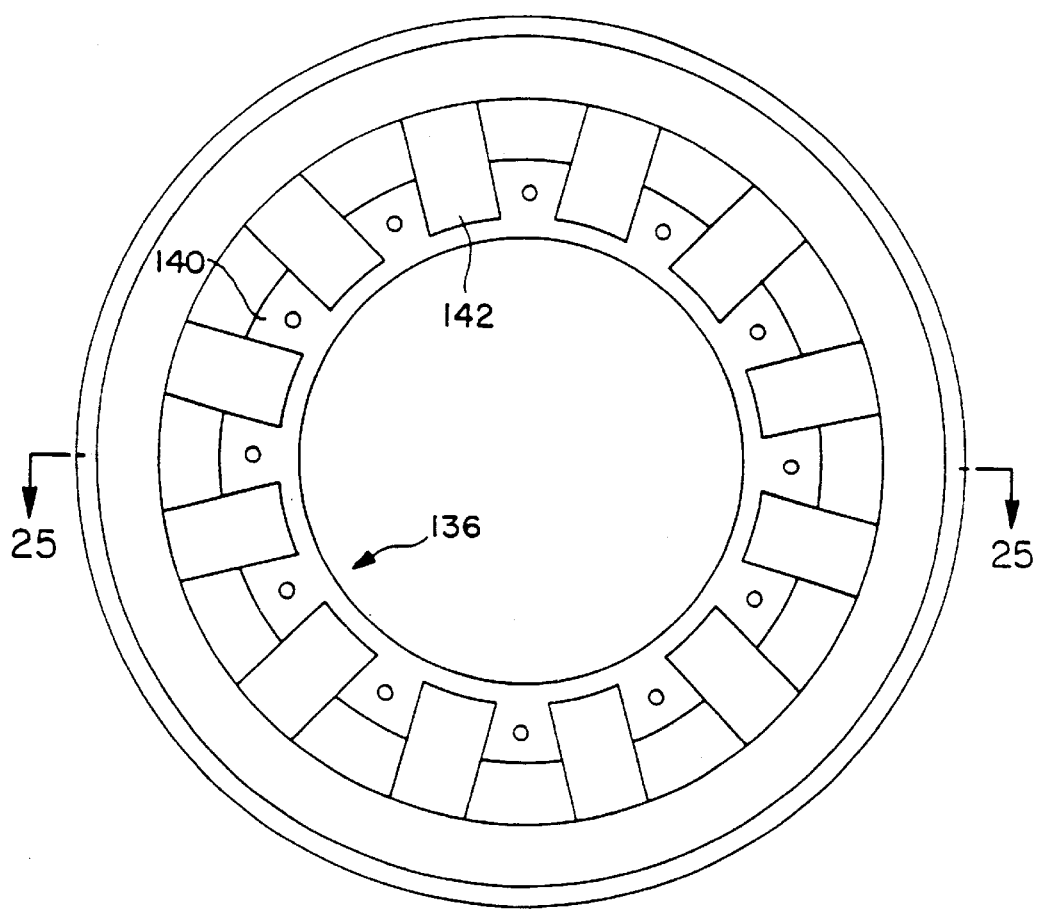
FIG. 24 is a bottom view of a vacuum device showing, in particular, an insert utilizing a number of pins for engaging the anterior surface of the eye during the eye surgery.
Figure 30:
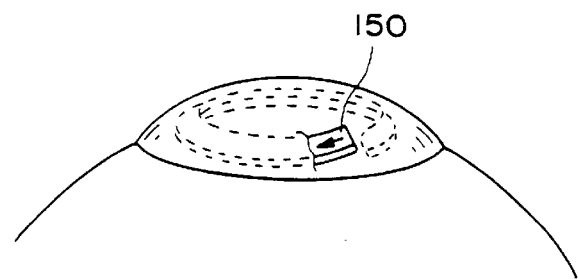
Figure 31:
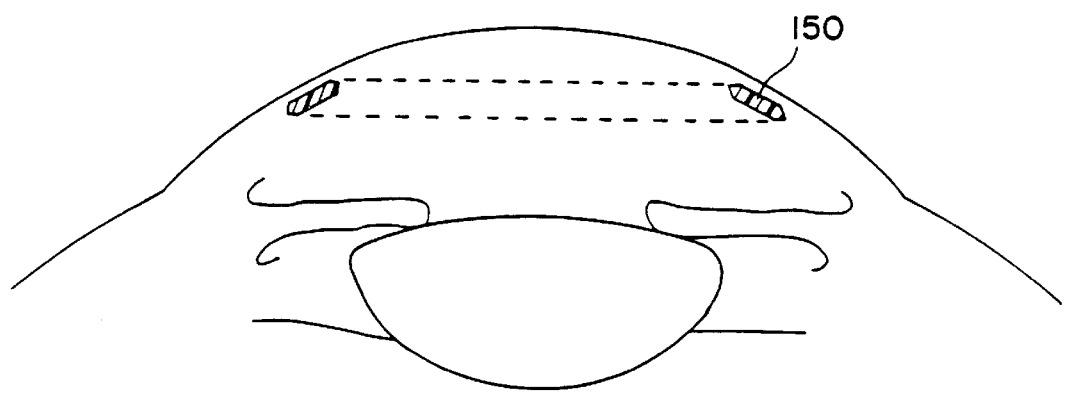
FIG. 31 shows the positioning of the ICR in the stroma.

FIGS. 24 and 25 show another variation in which an insert (136) containing a number of pins (138) may be included as an integral portion of the support base (50). FIG. 24 shows a bottom view of the ring as it is placed within the bottom portion of the support base (50). The insert ring (136) contains a surface (140) which serves as the inner wall of the circumcorneal vacuum chamber (142). In this variation of the invention, pins (138) extend for a short distance through that sloping wall (140) so that as vacuum is introduced into chamber (142), the pins engage the eye and penetrate a short distance into the cornea. The insert ring may also include slots (142) to allow the vacuum to be distributed geometrically about the pins with a bit more regularity. The insert ring (136) may be placed in a chamfer within the interior surface of support base (50) as is shown in a cross-section in FIG. 25. As is shown in FIG. 25, the surface of the insert ring which meets the anterior cornea (140) is, or may be, sloped in the same fashion as is the anterior wall (108) found in FIGS. 17 and 18. Incidentally, the outer vacuum chamber wall (144) is shown in cross-section in FIG. 25 to have a square shoulder. It has been observed that this configuration causes only minimal trauma when used in this inventive device with an appropriate amount of vacuum. The trauma is seen to be even less than that observed with vacuum chamber outer walls (106) such as is shown in FIG. 17.

These combinations of vacuum chambers, vanes and ridges within the vacuum chamber, insert rings with and without pins, all serve to prevent the rotation of the device during the ophthalmic operation for which this device is intended. Furthermore, the use of the insert ring helps to prevent twisting of the corneal surface during insertion of the dissector blade, as explained below.

Operation of the Inventive Device

FIGS. 26–29 show the process for using the combination device.

FIG. 26 shows a combination of support base (50) and corneal centering and fixation guide (62) placed on the front of a patient's eye (146). The surgeon centers the device on the eye using reticle (82). At this point, vacuum has not been applied to the circumcorneal vacuum ring (52). However, as soon as the device is considered to be centered, vacuum is applied as is shown in FIG. 27 through vacuum source line (58). The amount of vacuum applied is known. The corneal centering and fixation guide (62) is then removed from support base (50). It may be observed that within circumcorneal vacuum ring (52) is a slight bulging of the eye. This bulging of the eye contacts the vanes within the vacuum chamber; such vanes are discussed with relation to FIGS. 3, 4, 20, 21, 22 and 23, and the insert ring shown in FIGS. 24 and 25. This contact with the vanes helps prevent rotation or other movement of the support base (50). Once the support base is firmly affixed to the eye, the lance (68) is brought through the window in the support base to produce a small incision (148) in the cornea. The incision extends through epithelium and Bowman's membrane and is approximately 1–2 mm long and about 0.2 mm deep. The incision is on a radius of the cornea. A small spatula which fits into incision (148) may be used to make an initial separation in the inner lamellar layers at the bottom of incision (148) within the stroma. This "teasing" of the lamella will facilitate the insertion of the dissector blade (66). It should be noted at this point that the large viewing port (54) promotes ease of viewing for the surgeon onto the cornea particularly when used in conjunction with the large ID bore of the support base (50).

Finally, dissector barrel (64) is introduced into the support base (50). The dissector blade (66) is introduced into the cornea through incision (148) and turned until dissector blade support arm (84) nears the incision (148). When the support arm reaches the incision, the rotation of dissector barrel (64) and attached dissector blade (66), it is reversed and the dissector blade is backed out of the inner subsurface lamellar tunnel it has formed. The vacuum is then eased and support base (50) is removed from the eye. Once the inventive device is removed from the eye, the ICR (150) may be introduced into the intrastromal channel just produced desirably with a coating of hyaluronic acid or other suitable material as a lubricant. The ends of ICR (150) may be joined using techniques discussed in the patents discussed above.

This invention has been described and exemplified in some detail. Those having ordinary skill in this art would recognize variations and equivalents which would be well within the scope of the invention disclosed here but perhaps outside the scope of the appended claims. It is applicants' intention that these equivalent variations be included within the scope of this invention.

We claim as our invention:

1. A corneal vacuum centering guide and dissector assembly comprising a support base having a proximal end; a distal end; a central section extending between the proximal and the distal ends, said central section having a wall with a generally cylindrical bore having a central axis, a length and a diameter where the ratio of the length to the diameter is between about 0.25:1 and 15:1, said wall having an opening extending from said bore through said wall, and an annular vacuum chamber located at the proximal end and adapted to create an annular vacuum space when placed against the eye.

2. The assembly of claim 1 in which the annular vacuum chamber has an inner wall and an outer wall and at least one of the inner and outer walls have integral ridges or vanes which are adapted to extend down to and contact the eye during use.

3. The assembly of claim 2 in which the vacuum chamber contains integral ridges.

4. The assembly of claim 2 in which the vacuum chamber contains radial vanes.

5. The assembly of claim 1 in which the ratio is between 0.4:1 and 1:1.

6. The assembly of claim 1 in which the ratio is at least 1:1 and less than about 3:1.

7. The assembly of claim 1 in which the ratio is at least 3:1 but less than about 15:1.

8. The assembly of claim 1 in which the vacuum chamber contains an insert detachably mounted to the proximal end of the support base which insert contains short pins mounted to engage the cornea during use.

9. The assembly of claim 1 additionally comprising a corneal centering and fixation guide having an outer diameter which slidably fits within the cylindrical bore of the support and a reticle coincident with the central axis of the support base.

10. The assembly of claim 1 additionally comprising a knife adapted to place a small incision in the eye.

11. The assembly of claim 9 additionally comprising a viewing port through the central section wall.

12. The assembly of claim 1 additionally comprising a dissector assembly having a body sized to fit within said cylindrical bore, a dissector in the form of a major arc having a dissecting end and a support end and a dissector support connecting said dissector to said body.

13. The assembly of claim 12 wherein said body additionally comprises a central bore having an inside diameter, said inside diameter is greater than the diameter of said major arc.

14. A corneal vacuum centering guide and dissector assembly comprising:

a support base having a proximal end; a distal end; a central section extending between the proximal and the distal ends and an annular vacuum chamber;

said central section having a closed-end wall, the inside of said closed-end wall forming a generally cylindrical central bore;

said annular chamber formed between said closed-end wall and an outer chamber wall; and a plurality of vanes within said annular chamber configured to engage the eye and resist rotation of said support base during use.

15. The assembly of claim 14 wherein said vanes are recessed within said annular chamber such that said vanes engage the eye only after vacuum is applied to said chamber.

16. The assembly of claim 14 wherein said closed-end wall further comprises an opening into said central bore.

* * * * *